United States Patent [19]

Saari et al.

[11] 4,082,845
[45] Apr. 4, 1978

[54] 3-(1-PIPERAZINYL)-PYRIDO[2,3-b]PYRAZINES

[75] Inventors: Walfred S. Saari, Lansdale; William C. Lumma, Jr., Pennsburg, both of Pa.

[73] Assignee: Merck & Co., Inc., Rahway, N.J.

[21] Appl. No.: 790,362

[22] Filed: Apr. 25, 1977

[51] Int. Cl.² .................. A61K 31/495; C07D 295/12
[52] U.S. Cl. ............................. 424/250; 260/268 BC; 260/250 BC
[58] Field of Search .................. 260/268 BC; 424/250

[56] References Cited

FOREIGN PATENT DOCUMENTS 1,440,722  6/1976  United Kingdom.

*Primary Examiner*—Paul M. Coughlan, Jr.
*Attorney, Agent, or Firm*—Rudolph J. Anderson, Jr.; Mario A. Monaco; Martin L. Katz

[57] ABSTRACT

3-(1-Piperazinyl)-pyrido[2,3-b]pyrazines and pharmaceutically acceptable salts thereof have serotoninmimetic activity. They are prepared by treating 3-halopyrido[2,3-b]pyrazines with piperazine.

5 Claims, No Drawings

3-(1-PIPERAZINYL)-PYRIDO[2,3-b]PYRAZINES

BACKGROUND OF THE INVENTION

This invention is concerned with 3-(1-piperazinyl)-pyrido[2,3-b]pyrazines and pharmaceutically acceptable salts thereof which demonstrate serotoninmimetic activity and hence are useful as anorectic, antidepressant, analgesic and hypnotic agents.

Several piperazinyl heterocycles are known in the art, for example, 2-(1-piperazinyl)quinoxalines (British Pat. No. 1,440,722); 4-(1-piperazinyl)quinazolines (U.S. Pat. No. 3,470,182); 2-(1-piperazinyl)quinolines (Rodriquez et al., European Journal of Pharmacology 24, 164-171 (1973); 4-(1-piperazinyl)cinnolines (U.S. Pat. Nos. 3,265,693 and 3,172,818); and 2-(1-piperazinyl)-pyrazines (Belgian Pat. No. 840,904). With this invention there is provided a group of 3-(1-piperazinyl)-pyrido[2,3-b]pyrazines with serotoninmimetic properties and which exhibit anorectic antidepressant, analgesic and hypnotic activity. There are also provided processes for preparing the novel compounds, pharmaceutical compositions comprising the novel compounds, and methods of treatment comprising the administration of such compounds and compositions.

DETAILED DESCRIPTION OF THE INVENTION

The novel compounds of this invention have structural formula:

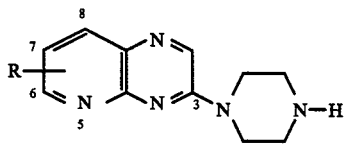

or a pharmaceutically acceptable salt thereof, wherein
R is hydrogen, halo, such as chloro, bromo, or fluoro, trifluoromethyl, lower alkyl, especially $C_{1-3}$ alkyl, lower alkylthio, especially $C_{1-3}$ alkylthio, lower alkoxy, especially $C_{1-3}$ alkoxy, or cyano.

In a preferred embodiment of the novel compounds, R is on the 6- or 7-position.

Also included within the scope of the present invention are non-toxic pharmaceutically acceptable salts. Such acid addition salts of the novel compounds are formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, sulfuric acid, phosphoric acid, nitric acid, isethionic acid or the like.

The novel process of this invention comprises reacting a pyrido[2,3-b]pyrazine substituted in the 3-position with a suitable leaving group such as a halogen, trialkylammonium, alkylsulfonyl, phenylsulfonyl, alkylsulfinyl or phenylsulfinyl, with piperazine. The 3-substituted-pyrido[2,3-b]pyrazine, preferably a 3-chloro compound, and piperazine are mixed in a solvent, and allowed to react until the reaction is essentially complete. The solvent used as the reaction medium is preferably a polar organic solvent such as acetonitrile, oxygenated solvents such as lower alkanols comprising methanol, ethanol, n-propanol, isopropanol, butyl alcohols, nitrogen containing solvents such as N,N-diloweralkylamides as, for example, dimethylacetamide, dimethylformamide, or mixtures of such materials.

The reaction is conducted at a temperature of from 0°-100° C. or at the reflux temperature of the reaction medium for a period of from 15 minutes to 24 hours. A period of from 10-24 hours at a temperature of from 15°-50° C. is preferred, and especially 20°-25° C.

A further embodiment of this invention is a method of producing an anorectic effect in patients in need of such treatment that comprises administering a therapeutically effective amount of the compounds and compositions of the present invention. Typically the dosage level ranges from about 0.1 to about 500 mg./day, and preferably is from 0.1 to about 100 mg./day of the active principle of the present invention.

The compounds of this invention also find utility as antidepressants, analgesics and hypnotic agents and for such purposes are administered as described above. Pharmaceutical compositions comprising a novel compound as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from about 0.1 to about 100 mg.

EXAMPLE 1

3-(1-Piperazinyl)-pyrido[2,3-b]pyrazine hydrogen fumarate hydrate

Step A: Preparation of 3-hydroxypyrido[2,3-b]pyrazine hydrochloride hydrate

A mixture of 10.9 g. (0.10 mol) of 2,3-diaminopyridine, 11.5 g. of glyoxylic acid hydrate (0.125 mol) and water (50 ml.) is stirred at 20°-25° C. overnight under $N_2$. The mixture is filtered and the cake is triturated with 31 ml. of concentrated hydrochloric acid. The solid which dissolves and recrystallizes is collected and washed with concentrated hydrochloric acid and tetrahydrofuran. After drying under vacuum at 50° C., 14.9 g. of 3-hydroxypyrido[2,3-b]pyrazine hydrochloride hydrate m.p. >320° C. is obtained.

Step B: Preparation of 3-chloropyrido[2,3-b]pyrazine hydrochloride

To 7.5 ml. of cooled and stirred N,N-dimethylformamide is added 9 ml. of phosphorus oxychloride followed by 5.5 g. (.030 mole) of 3-hydroxypyrido[2,3-b]pyrazine hydrochloride. The exothermic reaction is kept between 25°-68° C. for one hour, diluted with $CH_2Cl_2$ and filtered to give 3.3 g. of 3-chloropyrido[2,3-b]pyrazine hydrochloride, m.p. dec. >360° C.

Step C: Preparation of 3-(1-piperazinyl)-pyrido[2,3-b]pyrazine hydrogen fumarate hydrate A solution of 3.0 g. (0.015 mol) of 3-chloropyrido[2,3-b]pyrazine hydrochloride in 25 ml. of acetonitrile is treated with 6.0 g. (0.070 mol) of piperazine and stirred overnight at 20°-25° C. After concentrating under vacuum, the residue is partitioned between $CH_2Cl_2$ and aqueous NaOH. The $CH_2Cl_2$ extract is dried ($Na_2SO_4$), filtered and concentrated under vacuum to an oil which is dissolved in 30 ml. of absolute ethanol. The filtered ethanol solution is treated with 35 ml. of 0.4 molar fumaric acid in ethanol (95%) to give 2.0 g. of 3-(1-piperazinyl)-pyrido[2,3-b]-pyrazine hydrogen fumarate hydrate, m.p. 175°–176° C. dec.

Employing the procedure substantially as described in Example 1, but substituting for the 2,3-diaminopyridine used in Step A thereof, an equimolecular amount of:

- 5-chloro-2,3-diaminopyridine,
- 5-trifluoromethyl-2,3-diaminopyridine,
- 5-methyl-2,3-diaminopyridine,
- 5-methylthio-2,3-diaminopyridine,
- 6-trifluoromethyl-2,3-diaminopyridine, or
- 6-cyano-2,3-diaminopyradine there is produced, respectively

- 7-chloro-3-(1-piperazinyl)pyrido[2,3-b]pyrazine,
- 7-trifluoromethyl-3-(1-piperazinyl)pyrido[2,3-b]pyrazine,
- 7-methyl-3-(1-piperazinyl)pyrido[2,3-b]pyrazine,
- 7-methylthio-3-(1-piperazinyl)pyrido[2,3-b]pyrazine,
- 6-trifluoromethyl-3-(1-piperazinyl)pyrido[2,3-b]pyrazine, or
- 6-cyano-3-(1-piperazinyl)-pyrido[2,3-b]pyrazine as the hydrogen fumarate salt, in accordance with the following synthetic scheme:

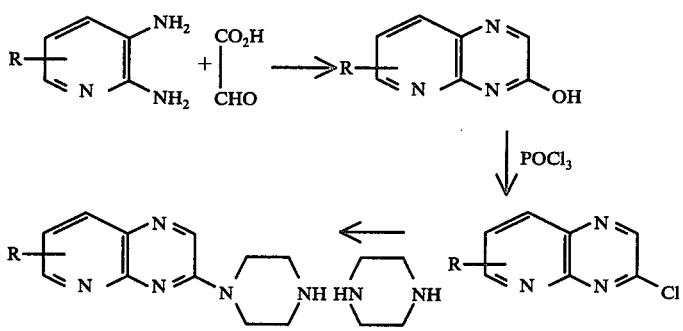

EXAMPLE 3

Preparation of Capsule Formulation

| Ingredient | Milligrams per Tablet |
|---|---|
| 3-(1-piperazinyl)-pyrido[2,3-b] pyrazine hydrogen fumarate hydrate | 6 |
| Starch | 87 |
| Magnesium stearate | 7 |

The active ingredient, starch and magnesium stearate are blended together. The mixture is used to fill hard shell capsules of a suitable size at a fill weight of 100 milligrams per capsule.

EXAMPLE 4

Preparation of Tablet Formulation

| Ingredient | Milligrams per Tablet |
|---|---|
| 3-(1-piperazinyl)-pyrido[2,3-b] pyrazine hydrogen fumarate hydrate | 12 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° C. The dry granules are passed through a No. 16 screen. The mixture is lubricated with magnesium stearate and compressed into tablets in a suitable tableting machine. Each tablet contains 12 milligrams of active ingredient.

What is claimed is:

1. A compound of structural formula:

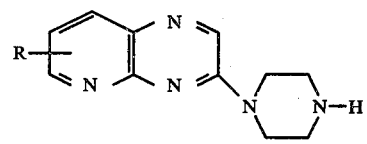

or a pharmaceutically acceptable salt thereof, wherein R is hydrogen, halo, trifluoromethyl, lower alkyl having from 1 to 3 carbon atoms, lower alkylthio having from 1 to 3 carbon atoms, lower alkoxy having from 1 to 3 carbon atoms or cyano.

2. The compound of claim 1 wherein R is the 6- or 7-position, or a pharmaceutically acceptable salt thereof.

3. The compound of claim 1 which is 3-(1-piperazinyl)-pyrido[2,3-b]pyrazine or a pharmaceutically acceptable salt thereof.

4. A method of producing an anorectic effect in a patient in need of such treatment comprising the administration of an effective amount of a compound of structural formula:

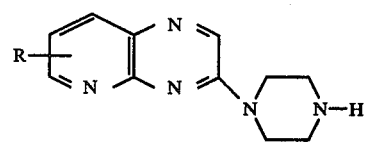

or a pharmaceutically acceptable salt thereof, wherein R is hydrogen, halo, trifluoromethyl, lower alkyl having from 1 to 3 carbon atoms, lower alkylthio having from 1 to 3 carbon atoms, lower alkoxy having from 1 to 3 carbon atoms or cyano.

5. A pharmaceutical anorectic composition comprising a pharmaceutical carrier and an effective amount of a compound of structural formula:

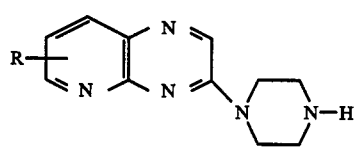
or a pharmaceutically acceptable salt thereof, wherein R is hydrogen, halo, trifluoromethyl, lower alkyl having from 1 to 3 carbon atoms, lower alkylthio having from 1 to 3 carbon atoms, lower alkoxy having from 1 to 3 carbon atoms or cyano.
* * * * *